United States Patent [19]
Oblad et al.

[11] Patent Number: 4,950,908
[45] Date of Patent: Aug. 21, 1990

[54] FLOCCULANT CONTROL SYSTEM

[75] Inventors: Hayward B. Oblad; Gary F. Meenan, both of Bethel Park, Pa.

[73] Assignee: Consolidation Coal Company, Pittsburgh, Pa.

[21] Appl. No.: 448,500

[22] Filed: Dec. 11, 1989

Related U.S. Application Data

[62] Division of Ser. No. 325,837, Mar. 20, 1989.

[51] Int. Cl.$^5$ ............................................. G01N 15/07
[52] U.S. Cl. ..................................... 250/574; 356/442
[58] Field of Search ................ 250/574, 573; 356/442, 356/338, 339, 340, 341, 342

[56] References Cited

U.S. PATENT DOCUMENTS

| 3,650,698 | 3/1972 | Adler | 356/442 |
| 4,797,550 | 1/1989 | Nelson et al. | 250/574 |
| 4,797,559 | 1/1989 | Oblad et al. | 250/574 |

Primary Examiner—David C. Nelms
Assistant Examiner—Que Tan Le
Attorney, Agent, or Firm—Alan McCartney

[57] ABSTRACT

A control system having opto-electric detectors responsive to different solids concentrations and character of the solids of a slurry, the output of the detectors controlling the addition of a flocculants to the slurry to optimize coagulation of the materials in the slurry. The detectors having outputs sensing different slurry conditions with the detector outputs being processed to control the addition of different flocculants to the cell.

3 Claims, 2 Drawing Sheets

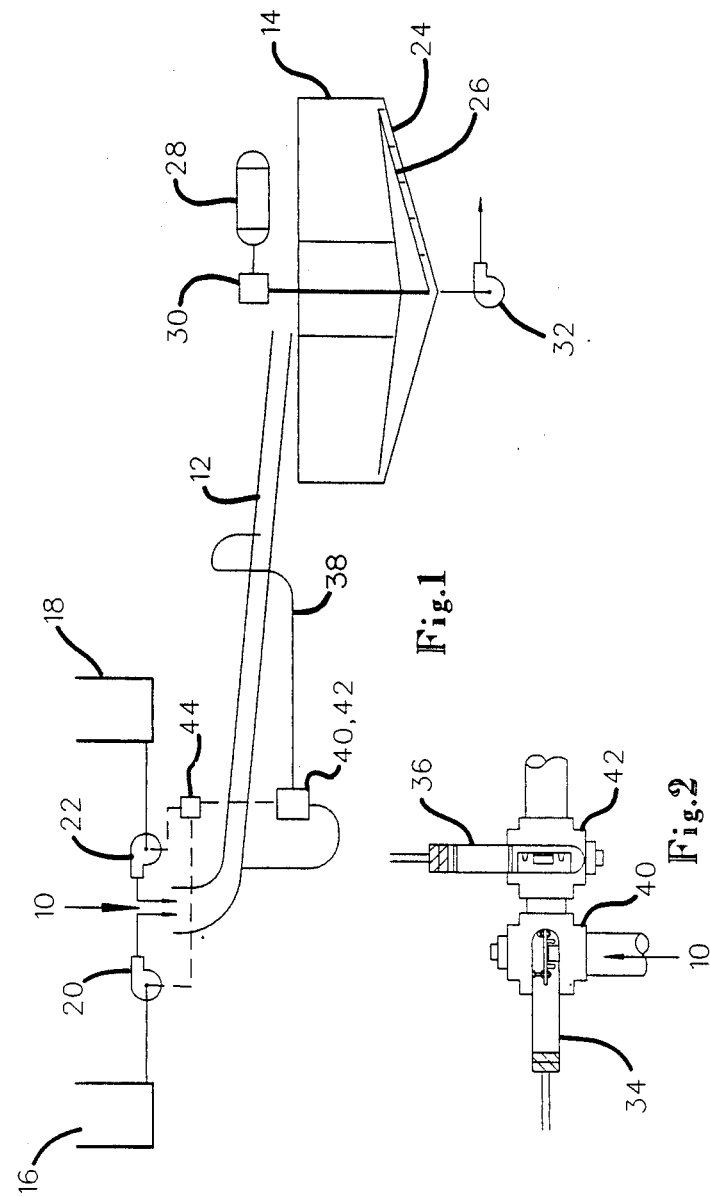

FLOCCULANT CONTROL SYSTEM

This is a divisional of copending application Ser. No. 325,837 filed on Mar. 20, 1989.

BACKGROUND OF THE INVENTION

1. Field of the Invention

This invention relates to a method and apparatus for controlling the supply of flocculants to a slurry mixture to coagulate various solids in the slurry.

2. Summary of the Prior Art

In the processing of coal, a feed stream comprising a slurry of coal fines and clay is passed to a thickener or clarifier to which anionic flocculant is added to coagulate the coal fines and cationic flocculant is added to coagulate the clay so that the resulting solids can be separated from the water so that the water can be disposed of or reused in the coal processing.

This type of apparatus for separating solids from liquids may take the form of a large container having a rotary driven rake for moving the agglomerated sludge material from the bottom to an outlet and a weir for removing the clarified water from the top. In many material processing systems, such as coal cleaning, it is desirable to automatically control the addition of the flocculants to the system in response to the concentration and character of the solids in the system.

In prior art devices, a determination of an increase in solids concentration in the slurry will result in an increase in the addition of both flocculants to the slurry which is undesirable since it may be that only one solid, either coal or clay has increased in concentration in the slurry. Thus, it is desirable to know which of the solids of the slurry has increased or decreased in concentration so that the proper flocculant supplied to the slurry can be controlled.

In this area, attempts have been made to determine the character of solids in a coal slurry. A Cendrex continuous ash monitor, developed by the Dutch State Mines, employs a beam of X rays from a cobalt X-ray tube. The beam is split into two equal parts by a rotary chopper, one part striking the coal sample and the other striking a reference of Plexiglas. Because of the difference in absorption coefficients of the coal and the Plexiglas, the intensities of the reflected beams generally are different. This difference is translated by means of a photocell into clay content values for the coal sample.

Another such device was developed by the National Coal Board and the Atomic Energy Research Establishment in Great Britain. This device utilized a radiation source to monitor clay content of a sample slurry. The radiation emitted bombards the surface of the coal, and is either absorbed or backscattered, depending on the elements present in the sample. Elements of low atomic number (the combustible elements) backscatter well, whereas elements of a higher atomic number (clay) absorb the radiation. By measuring the backscattered radiation, a determination of the clay content of the coal sample can be made.

A simple inexpensive system for determining the coal and clay content of a slurry to control the addition of flocculant to a processing cell has not, however, been previously developed.

SUMMARY OF THE INVENTION

It is the purpose of this invention to provide a control system for the addition of flocculants to a feed stream from which solids are removed from a slurry.

It is an object of this invention to provide a control system having detectors responding differently to solids concentrations and character of the solids of a feed stream, the signals from the detectors being fed to a digital process controller which calculates solids concentration and character of the solids to adjust variable speed pumps controlling the addition of flocculants to the feed stream which passes to a cell in which the feedstream solids are coagulated to separate the solids from the liquid.

It is another object of this invention to provide detectors responsive to the change in light backscattered from a slurry to indicate the solids concentration and nature of the solids in the slurry, with the detectors being responsive in different manners to the solids concentration and nature of the solids, the signal output can be processed by a controller to determine which solid concentration has varied, and control the addition of a particular flocculant to the slurry to coagulate that particular solid.

It is also an object of this invention to provide detectors unequally responsive to the solids concentration of a slurry and clay content of the solids, the output of the detectors being processed to determine the change of the solids concentration and the nature of the solids in the slurry to control the addition of additives to the slurry.

It is a further object of this invention to provide a opto-electronic device for detecting the character of the solids in slurry, the detector comprising light-emitting diodes and a photoconductor separated by an opaque collar; the detector being mounted on a solid support insertable into a glass tube and adapted to be reinsertable in other glass tubes without altering the function of the detector.

BRIEF DESCRIPTION OF THE DRAWINGS

FIG. 1 is a diagramic illustration of the control system of this invention;

FIG. 2 is an illustration of the detectors of this invention;

DESCRIPTION OF THE PREFERRED EMBODIMENT

Figure 4:
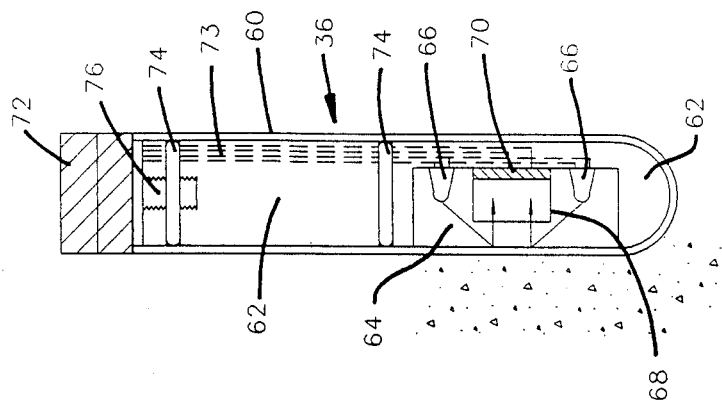
FIG. 4 is an illustration of the detector responsive to the character of the solids in a slurry feed stream.

This invention relates to an extension of the technology disclosed in commonly owned U.S. Pat. No. 4,797,559 in which an opto-electronic detector determines the character of solids in a slurry and adjusts the flow rate of additives to a flotation cell to maximize cell performance. In this invention, opto-electronic detectors of two types are used, each being responsive to the detecting slurry solids concentration and the character of the solids in the slurry. The first detector is more or less responsive to the solids concentration and character of the slurry than the second detector. The output of the detectors is used to adjust the addition of different additives to the slurry to optimize solids settling from the slurry. This new development is shown applied to the operation of a processing cell such as a thickener used in coal processing, however, it should be appreciated that the method and apparatus could be utilized in any processing of a feed stream from which various solids are coagulated in a processing cell.

As illustrated in FIG. 1, the novel control system and components thereof of this invention are illustrated being used with a thickener or clarifier to control the addition of flocculant to coagulate the fines of a slurry. A thickener feed stream 10 passes through a conduit 12, for example, to the thickener 14. Tanks 16 and 18 contain cationic and anionic flocculant, respectively, which are fed by variable speed pumps 20, 22 to the feed stream 10 to coagulate the feed stream fines in the thickener.

The thickener 14 comprises a large container 24 containing a rake 26 rotationally driven by a motor 28 through gear box 30. The rotation of rake 26 moves the coagulated slurry fines to the underflow pump 32, while the clarified water of the feed stream is removed from the upper portion of the thickener.

FIG. 2 illustrates the detectors 34, 36 which are located in the bypass stream 38 (see FIG. 1). The thickener stream 10 passes into the housing 40 of the first detector 34 and then into the housing 42 of the second detector 36 and back into the conduit 12. The signals from the detectors 34, 36 are fed to the digital process controller 44 which adjusts the variable speed pumps 20, 22 to provide the correct amount of flocculants to the feed stream.

Figure 3:
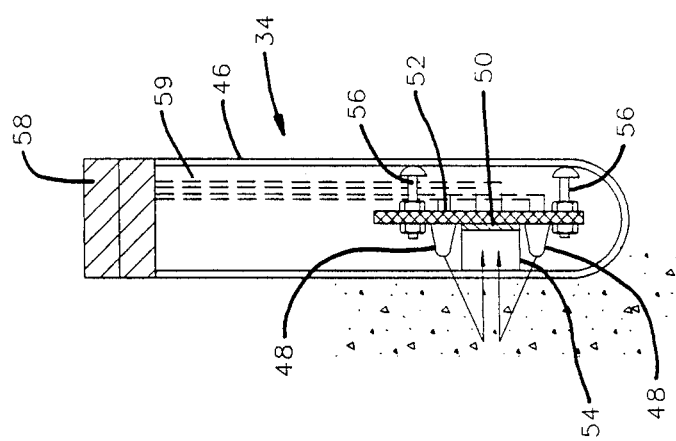
FIG. 3 is an illustration of the solids concentration detector of this invention.

Attention is now directed to FIG. 3 which illustrates the detector 34 which is sensitive to both the solids concentration of the feed stream and clay content of the feed solids and FIG. 4 which illustrates the detector 36 which is mostly sensitive to the clay content of the feed solids. The detector 34 comprises a glass tube 46 housing light emitting diodes (LED's) 48 and photoconductor 50 supported on a board 52. An opaque collar 54 is positioned between the LED's 48 and the photoconductor 50 so that the light emitted passes into the feed stream and is reflected back (backscattered) to the photoconductor 50. The board 52 is supported by adjustable posts 56 so that the collar 54 can be positioned against the surface of the tube 46 so that the emitted light must travel into the feed stream to be reflected. The open end of the collar is shaped to match the inner surface of the tube. This permits this detector to be highly sensitive to the concentration of the solids in the feed stream. If the feed stream has a high coal concentration, more light will be absorbed by the feed stream and less light will be reflected to the photoconductor increasing the photoconductor resistance by an order of magnitude. The second detector also sees the increase in coal content but differently than the first detector. These signal the process controller to adjust the pump speed to add anionic flocculant to the feed stream to further agglomerate the coal fines in the thickener. Likewise, should the feed stream coal content decrease, more light will be reflected decreasing the resistances of the photoconductors to signal the controller to adjust the speed of pump 22 to add less anionic flocculant to the feed stream. A stopper 58 encloses the end of tube 46 and the wires 59 from the LED's and photoconductor pass through the stopper and are connected at the processor.

Attention is now directed to FIG. 4 which illustrates the detector 36 which is less sensitive to the slurry solids concentration but responsive to the change in clay content of the solids. The detector 36 comprises a glass tube 60 into which a support 62 is positioned. The support follows the contour of the glass tube and has a recess 64 onto which the LED's 66, collar 68 and photoconductor 70 are positioned. A wire way 73 passes through the support 62 and out the stopper 72 permitting the wires to be connected to the controller. O-rings 74 are provided around the support 62 to securely mount the support 62 in the tube 60. A threaded opening 76 in the end of support 62 permits a bolt to be secured to the support 62 for removal of the support 62 from the tube 60. In the environment of abrasive-type materials, the tube may become eroded requiring the detector to be removed from the tube and reinserted into a new tube for continued accurate functioning. Further, with the detecting elements being mounted on the support 62, reinsertion into a new tube will not change the relationship of the detecting elements resulting in different readings from the photoconductor.

The collar 68 in detector 34 is recessed from the inner surface of the tube 60. When the collar is recessed from the glass, light bounces from the wall of the glass tube into the collar. In effect, the glass acts as a mirror that has a backing that changes reflectivity with solids/clay content. Light reflects to the photoconductor off the slurry/glass interface and the inner wall of the tube. Since the light which bounces off the inner wall of the tube does not depend on slurry quality, it illuminates the photoconductor constantly and limits the variance in the resistance which is achieved. Thus, this type of detector is less sensitive than detector 34 in which the collar contacts the glass. In the event the clay content of the solids changes (thus slurry color changes), then the change of the reflectivity from the surface of tube 60 will change the output of the photoconductor which through the controller will alter the amount of flocculants added to the feed stream.

Both detectors are responsive to a change in solids concentration and the nature of the solid which changed in concentration based upon the reflection of the light from the slurry to effect the resistance of photoconductor in the sensors. Because the sensors are responsive in different manners, a reading can be obtained of the specific solid which has changed in concentration, and thus the proper flocculant can be increased or decreased as required.

For example, should the solid concentration increase as a result of increase in coal concentration, less light is reflected (FIG. 3 unit) increasing the resistance of photoconductor 50. At the same time, the photodetector 70 of FIG. 4 would also see the increased coal content (less reflectance) and the sensor inputs would be combined in the controller which would cause the anionic flocculant to be supplied and the cationic flocculant supply would stay the same. Should the increased solids concentration result from an increased clay concentration of the slurry more light would be reflected to the FIG. 3 detector decreasing the resistance of the photoconductor. Since the FIG. 4 detector is more responsive to change in slurry color—clay content—there would be a more significant decreases in the resistance of photoconductor 70. The determination of which solid increased in concentration can be accomplished by one detector strongly responsive to both solids concentration of the slurry and the clay content of the solids (detector 34) and another detector moderately responsive to clay content and weak in response to the solids concentration of the slurry (detector 36).

However, in any given period of time, the change in solids concentration will be caused by an increase or decrease of either the clay or coal concentration simultaneously and because the detectors read not only the change in solids concentration but also the nature of the solids change in different signal outputs, all parameters of change are determined in the controller. By having two variables—coal content, clay content and two sensors, each responsive to a change in the variables in different fashions, all parameters of change are simultaneously seen by both sensors which signal the controller which determines the change and controls the pumps.

It should be noted that in the case of both detectors, the sensing functions through the side of the glass tube where there is a consistent glass property rather than the end of the tube which when formed does not have consistent translucent properties which would affect detector function. Thus, it can be seen that the rate of addition of the flocculants to a feed stream to a thickener can be controlled by knowing the solids concentration and character of the solids. In coal plants anionic flocculant is usually added in proportion to the mass flow of carbonaceous material reporting to the thickener and cationic flocculant is added in proportion to the mass flow of clay. The mass flows of the two materials can be estimated by determining the overall solids concentration of the slurry and the clay content of the solids. The feed rate of slurry normally remains constant to a thickener. By using the two types of opto-electronic devices, each with differing sensitivities to the solids concentration and clay content of the solids, a control system for flocculant addition is obtained.

With detector 34 being more sensitive to solids concentration than detector 36, the signals from the two detectors are fed to a digital process controller which calculates the solids concentration of the slurry and the clay content of the solids. The controller then adjusts the variable speed pumps to provide the correct amounts of flocculants.

We claim:

1. An opto-electric detector having a tubular transparent housing receiving a platform mounting light emitting diodes and a photoconductor separated by an opaque shield extending toward the internal housing surface, including means to adjustably support said platform within said housing to vary the spacing between said shield and said surface.

2. An opto-electric detector having a tubular transparent housing receiving a support having a recess supporting a light emitting diode and a photoconductor separated by an opaque shield, the support surface conforming to the surface of the housing and being supported therein.

3. The opto-electric detector of claim 2 wherein said shield extends toward said housing and is spaced therefrom.

* * * * *